(12) United States Patent
Ishii et al.

(10) Patent No.: US 7,858,039 B2
(45) Date of Patent: Dec. 28, 2010

(54) TISSUE PIECE TREATING APPARATUS

(75) Inventors: Masaki Ishii, Kanagawa (JP); Hironobu Minai, Kanagawa (JP); Noriyuki Tanaka, Kanagawa (JP); Takashi Yamada, Kanagawa (JP)

(73) Assignees: Jokoh Co., Ltd. (JP); Yasuhiko Kitayama (JP); Kimihiko Yamada (JP)

( * ) Notice: Subject to any disclaimer, the term of this patent is extended or adjusted under 35 U.S.C. 154(b) by 0 days.

(21) Appl. No.: 12/670,521

(22) PCT Filed: Jul. 23, 2008

(86) PCT No.: PCT/JP2008/063183

§ 371 (c)(1),
(2), (4) Date: Jan. 25, 2010

(87) PCT Pub. No.: WO2009/014139

PCT Pub. Date: Jan. 29, 2009

(65) Prior Publication Data

US 2010/0206226 A1    Aug. 19, 2010

(30) Foreign Application Priority Data

Jul. 25, 2007   (JP) ............................ 2007-193503
Sep. 14, 2007   (JP) ............................ 2007-238602

(51) Int. Cl.
*B01L 3/00* (2006.01)
(52) U.S. Cl. ............................ 422/99; 422/62; 422/63; 422/64; 422/65; 422/100; 422/104; 435/40.51; 435/40.52; 436/46; 436/174
(58) Field of Classification Search ............ 422/62–65, 422/99–100, 104; 435/40.51, 40.52; 436/46, 436/174
See application file for complete search history.

(56) References Cited

U.S. PATENT DOCUMENTS 4,656,047 A    4/1987    Kok et al.

(Continued)

FOREIGN PATENT DOCUMENTS

DE    4019182 A1    1/1991

(Continued)

OTHER PUBLICATIONS

International Search Report for International Application No. PCT/JP2008/063183 mailed Oct. 7, 2008.

(Continued)

*Primary Examiner*—Jyoti Nagpaul
(74) *Attorney, Agent, or Firm*—Cantor Colburn LLP

(57) ABSTRACT

Provided is a tissue piece treating apparatus comprising an automatic controlling means for feeding back the temperature of the treatment liquid or molten paraffin in the bath inside detected by a temperature sensor to switch a heating mode and a cooling mode alternately to control the temperature; a heating means for turning OFF in an air-cooling fan of the ultrasonic vibrator and ON in a plane heater at the heating mode, thereby transferring the heat generated by the ultrasonic vibrator and the plane heater; and, a cooling means for turning ON in the air-cooling fan of the ultrasonic vibrator and OFF in the plane heater at the cooling mode, thereby blocking the heat transfer from the ultrasonic vibrator and the plane heater to the bath inside. These means can suppress the excessive heating of a tissue piece so that they can suppress the heating modification of the tissue piece.

5 Claims, 7 Drawing Sheets

U.S. PATENT DOCUMENTS

| | | |
|---|---|---|
| 4,839,194 A | 6/1989 | Malluche et al. |
| 5,089,288 A | 2/1992 | Berger |
| 5,244,787 A | 9/1993 | Key et al. |
| 5,281,516 A | 1/1994 | Stapleton et al. |
| 5,382,511 A | 1/1995 | Stapleton |
| 6,207,408 B1 | 3/2001 | Essenfeld et al. |
| 6,291,180 B1 | 9/2001 | Chu |
| 6,458,598 B1 | 10/2002 | Huang |
| 2002/0150510 A1 | 10/2002 | Lihl et al. |
| 2006/0120925 A1 | 6/2006 | Takayama et al. |

FOREIGN PATENT DOCUMENTS

| | | |
|---|---|---|
| EP | 1005633 B1 | 9/2008 |
| GB | 2233452 A | 1/1991 |
| JP | 2001-516869 A | 10/2001 |
| JP | 2004-538484 A | 12/2004 |
| JP | 2005-345197 A | 12/2005 |
| WO | 99/09390 A1 | 2/1999 |
| WO | 03/016872 A1 | 2/2003 |

OTHER PUBLICATIONS

Supplementary European patent Search Report for Application No./Patent No. 08791440.4-1234/2184598 dated Jun. 30, 2010.

TISSUE PIECE TREATING APPARATUS

CROSS REFERENCE TO RELATED APPLICATIONS

This is a U.S. national stage application of International Application No. PCT/JP2008/063183, filed on 23 Jul 2008. Priority under 35 U.S.C. §119 (a) and 35 U.S.C. §365 (b) is claimed from Japanese Application No. JP2007-193503, filed 25 Jul 2007, and from Japanese Application No. JP2007-238602, filed 14 Sep. 2007, the disclosures of which are also incorporated herein by reference.

TECHNICAL FIELD

The present invention relates to a tissue piece treating apparatus having a structure in which a treatment liquid or molten paraffin for treating a tissue piece accommodated in a cassette is stored in a bath inside in a treating bath, the tissue piece is soaked in the stored treatment liquid or molten paraffin and an ultrasonic vibrator is fixed to or brought into contact with the external wall outside the treating bath, and having a function of promoting impregnation of the treatment liquid or molten paraffin into the tissue piece or treatment thereof by irradiating an ultrasonic wave into the bath inside from the ultrasonic vibrator.

[Main Terms Used in Claims and Description]

[Tissue Piece]

The term "tissue piece" used in Claims and Description of the present application includes those produced or excised from human or experimental animal living tissues (including organs, blood vessel, blood and blood cell components, brain, nerve, lymph node, internal organs, tumor tissue, bone tissue, head hair, nail, skin and cultured tissues thereof). The shape thereof includes a block shape and a sliced strip shape.

[Treatment]

The term "treatment" used in Description of the present application includes an operation of carrying out a fixing treatment of a tissue piece with a fixing agent (fixing treatment), an operation of carrying out a dehydrating treatment of a tissue piece with a dehydrating agent (dehydrating treatment), an operation of carrying out a degreasing treatment of a tissue piece with a degreasing agent (degreasing treatment), an operation of carrying out an intermediate treatment (e.g., a treatment carried out between dehydrating and degreasing treatments and a paraffin impregnating treatment) of a tissue piece with an intermediate agent (intermediate treatment) and an operation of impregnating a tissue piece with a paraffin (paraffin impregnating treatment).

BACKGROUND ART

Conventionally, in fabrication of a tissue specimen for pathological diagnosis, a paraffin block is fabricated via steps of fixation, dehydration, de greasing, intermediate treatment, impregnation treatment with paraffin and the like, and the paraffin block is sliced, finally, stained by various staining methods, and covered with a cover glass to give a praeparate (prepared specimen) which is the observed by a microscope for pathological diagnosis.

Recently, speed up of the pathological diagnosis is required, and there are developed apparatuses for treatment of various tissue specimens in treatment steps for speed up of the treatment. Also for treatment apparatuses of conducting from a fixing treatment step to a paraffin impregnating treatment step, there are measures of shortening the treatment time, such as provision of pressurizing and pressure reducing mechanisms and a stirring function.

Nowadays, for speed up of the treatment, tissue piece treating apparatuses utilizing microwave energy as described in U.S. Pat. Nos. 4,656,047, 4,839,194 and 5,244,787 are also developed. However, since these technologies use the same design as for microwave ovens used for home cooking, these are utterly different from the technology applying an ultrasonic wave as in the present invention.

An invention according to U.S. Pat. No. 5,089,288 (hereinafter, referred to as "latest prior art") discloses an invention regarding a method of impregnation of a tissue piece with a paraffin. FIG. 1 shows a schematic sectional view of an impregnation treating bath used in the latest, prior art (FIG. 1 in U.S. Pat. No. 5,089,288).

Matters and drawings described in U.S. Pat. No. 5,089,288 can be derived directly and unambiguously in the Description of the present application.

In the schematic sectional view, (1) represents a treating bath, (2) represents a bath inside, (3) represents a tissue piece, (4) represents a cassette, (5) represents a constant temperature bath, (6) represents an ultrasonic vibrator, (7) represents a cover, (8) represent a liquid surface, (9) represents a connector, (10) represents a pipeline, (11) represents a filter, (12) represents a vacuum pump, (13 to 17) represent tanks, and (L) represents liquid level. The treatment and paraffin impregnation treatment of the tissue piece (3) are all conducted in the bath inside (2) of the treating bath (1).

[Basic Structure of Treating Apparatus]

In the treating bath (1), the bath inside (2) and a drug solution flown into the bath inside (2) can be maintained at a previously-set temperature by being over-coated by the constant temperature bath (5).

The constant temperature bath (5) is capable of performing heating, cooling, temperature regulation and temperature control of the bath inside (2) and drug solution with a heat medium (e.g., air and water) which has been appropriately heated, cooled, temperature-regulated or temperature-controlled.

The ultrasonic vibrator (6) installed to the treating bath (1) is capable of oscillating an ultrasonic wave having a wavelength of, for example, 35 to 50 kHz.

The output of the ultrasonic vibrator (6) is 120 watts (when the treating bath is small) to 1200 watts (when the treating bath is large), and can be varied in the range of 100 to several hundreds of watts. The ultrasonic vibrator (6) gives ultrasonic wave energy suitable for the tissue piece (3) and drug solution introduced into the bath inside (2).

The cover (7) on the upper side can perform air tight or vacuum sealing of the treating bath (1).

Each drug solution is introduced up to the liquid level of the bath inside (2) so as to keep a space between the cover (7) and the liquid surface. The connector (9) is installed at a position distant sufficiently from the liquid surface (8) and communicates with the pipeline (10) and the filter (11). The bath inside (2) sealed with the cover (7) can be pressure-reduced or evacuated by a vacuum pump (12).

[Structure of Cassette]

The cassette (4) is a box-shaped vessel having a netted bottom part and a netted cover, generally used for a paraffin-impregnation treatment or paraffin-embedding of a tissue piece (3). A drug solution flown into the bath inside (2) of the treating bath (1) enters through a mesh of the net of the bottom part and the cover and comes into contact with the tissue piece (3), thus, the tissue piece (3) can be treated.

[Constitution of Tank]

The tanks (13 to 17) are connected to the treating bath. The tank (13) stores a fixing agent (e.g., isopropyl alcohol) for the tissue piece (3), the tank (14) stores a first dehydrating treatment liquid (70 wt % isopropyl alcohol/30 wt % water solution) used for a partial dehydrating treatment, the tank (15) stores a second dehydrating treatment liquid (100 wt % isopropyl alcohol) used for an intermediate dehydrating treatment, the tank (16) stores a third dehydrating treatment liquid (100 wt % isopropyl alcohol) used for a complete dehydrating treatment, and the tank (17) stores a molten paraffin. Drug solutions in the tanks are maintained at respective previously-set temperatures. The set temperature of the tank (17) is, for example, a temperature (e.g., 58° C.) at which a paraffin can be kept at liquid state. The set temperatures of the tanks (13 to 16) are, for example, a temperature (e.g., 58° C.) lower than the boiling point (82.8° C.) of isopropyl alcohol under standard atmospheric pressure. The drug solution stored in the tanks (13 to 17) can be introduced into the bath inside (2) of the treating bath (1) or the drug solution can be returned to the tanks (13 to 17) from the bath inside (2) by a drug solution feeding system (not shown) composed of a pump, valve and pipeline.

[Summary of Treating Procedure of Tissue Piece]

The tissue piece (3) is subjected to a fixing treatment with a fixing agent in the tank (13), then, subjected to a partial dehydrating treatment with a first dehydrating treatment liquid in the tank (14), then, subjected to an intermediate dehydrating treatment with a second dehydrating treatment liquid in the tank (15), then, subjected to a complete dehydrating treatment with a third dehydrating treatment liquid in the tank (16), then, subjected to a paraffin impregnating treatment with a molten paraffin in the tank (17). By adopting such an operation procedure, it becomes possible to carry out a fixing treatment, dehydrating treatment and paraffin impregnating treatment of a tissue piece without necessity of conducting an intermediate treatment with an intermediate agent (treatment conducted between dehydrating and degreasing treatments and a paraffin impregnating treatment).

[Fixing Treatment of Tissue Piece]

A cassette (4) in which a tissue piece (3) is set is set in the bath inside (2), then, the bath inside (2) is sealed with the cover (7). After sealing, a fixing agent (e.g., isopropyl alcohol) is introduced from the tank (13) up to the liquid level (L) of the bath inside (2). The temperature of the fixing agent is raised, by the ultrasonic wave energy of the ultrasonic vibrator (6), up to a temperature (for example, 58° C.) at which a paraffin can be maintained in liquid state. After completion of the fixing treatment of the tissue piece (3), the fixing agent is returned to the tank (13).

[First Dehydrating Treatment of Tissue Piece]

After completion of the fixing treatment, a first dehydrating treatment liquid (70 vol % isopropyl alcohol/30 vol % water solution) is introduced from the tank (14) up to the liquid level (L) of the bath inside (2). Since treatment liquids prepared in the tanks (14 to 17) are maintained previously at a treatment temperature (for example, 58° C.), the isopropyl alcohol introduced is maintained already at a treatment temperature (for example, 58° C.). Partial dehydration of a tissue piece carried out by soaking into 70 vol % isopropyl alcohol is promoted by irradiation of the first dehydrating treatment liquid and the tissue piece (3) with an ultrasonic wave. After completion of the first dehydrating treatment, the first dehydrating treatment liquid is returned to the tank (14).

[Second Dehydrating Treatment of Tissue Piece]

After completion of the first dehydrating treatment, a second dehydrating treatment liquid (100 vol % isopropyl alcohol) is introduced from the tank (15) up to the liquid level (L) of the bath inside (2). Further dehydration and degreasing of the tissue piece (3) are promoted by irradiation of the second dehydrating treatment liquid and the tissue piece (3) with an ultrasonic wave. After completion of the second dehydrating treatment, the second dehydrating treatment liquid is returned to the tank (15).

[Third Complete Dehydrating Treatment of Tissue Piece]

After completion of the second dehydrating treatment, a third dehydrating treatment liquid (100 vol % isopropyl alcohol) is introduced from the tank (16) up to the liquid level (L) of the bath inside (2). Complete dehydration and degreasing of the tissue piece (3) are promoted by irradiation of the third dehydrating treatment liquid and the tissue piece (3) with an ultrasonic wave. After completion of the third dehydrating treatment, the third dehydrating treatment liquid is returned to the tank (16).

[Paraffin Impregnating Treatment of Tissue Piece]

After completion of the third dehydrating treatment, a molten paraffin is introduced from the tank (17) up to the liquid level (L) of the bath inside (2), and after the introduction, the treating bath (1) is sealed with the cover (7). The temperature of the molten paraffin is maintained at a temperature capable of keeping the liquid state of the paraffin, for example, at 58° C. After sealing of the treating bath (1) with the cover (7), the pressure of the bath inside (2) is reduced to a degree of vacuum of the order of 10 kPa by a vacuum pump (12).

It is desirable to perform this pressure reduction as quickly as possible, however, by irradiation with an ultrasonic wave during pressure reduction, the temperature of isopropyl alcohol in the bath inside (2) reaches the boiling point to promote evaporation thereof, thereby increasing the pressure reduction speed. Impregnation of the molten paraffin into the tissue piece (3) is promoted by irradiating the tissue piece (3) and the molten paraffin with an ultrasonic wave while maintaining the degree of vacuum of the bath inside (2). By performing pressure reduction of the bath inside (2) in the treating bath (1), the boiling point of isopropyl alcohol (the boiling point under standard atmospheric pressure is 82.8° C.) yet remaining in the tissue piece (3) lowers.

Since the boiling point of isopropyl alcohol under vacuum is lower than the treatment temperature (58° C. at which a paraffin is capable of maintaining liquid state), isopropyl alcohol vaporizes out of the tissue piece (3) under vacuum and passes through without being dissolved in the molten paraffin around the tissue piece (3), and is discharged via a connector (9). Therefore, the molten paraffin is not polluted with isopropyl alcohol. A void generated by evaporation of isopropyl alcohol out of the tissue piece (3) is substituted immediate with the molten paraffin.

Since the paraffin impregnating treatment can be carried out with leaving utterly no air bubble in the tissue piece (3), even a tissue containing air such as a lung tissue can be completely substituted with a paraffin. By such a process, it becomes possible to conduct the paraffin impregnating treatment and paraffin embedding of tissue piece (3) in an extremely short period of time. In the case of a very thin tissue piece having a thickness of 2 mm, the treatment is possible in only 20 to 30 minutes, and in the case of a thick tissue piece having a thickness of 3 to 4 mm, the treatment is possible in 1 to 1.5 hours. Irrespective of very short treatment time, the paraffin impregnating treatment and paraffin embedding can be carried out with extremely high quality, thus, a sliced piece suitable for a histological microscopic check can be provided.

[Recovery of Liquid Paraffin]

After completion of the paraffin impregnating treatment of a tissue piece, the molten paraffin is returned to the tank (17) from the bath inside (2). Since the molten paraffin is not polluted by isopropyl alcohol, there is no need of a special pollution check for the recovered isopropyl alcohol and the tank (17). It may be advantageous to add the paraffin to the tank in an amount corresponding to the use amount of the paraffin impregnated into the tissue piece (3), thus, this procedure is very economical.

[Fabrication of Paraffin Block of Tissue Piece]

After the paraffin impregnating treatment of the tissue piece (3), a paraffin block is fabricated by a usual method.

[Merit (1) in Latest Prior Art]

As a first merit in the latest prior art, there is no necessity of conducting an intermediate treatment with an intermediate agent (treatment conducted between dehydrating and degreasing treatments and a paraffin impregnating treatment), and in the case of a very thin tissue piece having a thickness of 2 mm, the treatment is possible in only 20 to 30 minutes, and in the case of a thick tissue piece having a thickness of 3 to 4 mm, the treatment is possible in 1 to 1.5 hours. Irrespective of very short treatment time, the paraffin impregnating treatment and paraffin embedding can be carried out with extremely high quality, thus, a sliced piece suitable for a histological microscopic check can be provided.

[Merit (2) in Latest Prior Art]

As a second merit in the latest prior art, reaching of the temperature of isopropyl alcohol in the bath inside to the boiling point and evaporation thereof are promoted to accelerate the pressure reduction speed, by irradiating an ultrasonic wave during pressure reduction in performing reduction of the pressure in the bath inside down to a degree of vacuum of the order of 10 kPa by a vacuum pump after sealing the treating bath with a cover.

[Merit (3) in Latest Prior Art]

As a third merit in the latest prior art, since the paraffin impregnating treatment can be carried out with leaving utterly no air bubble in the tissue piece, even a tissue containing air such as a lung tissue can be completely substituted with a paraffin. By such a process, it becomes possible to conduct the paraffin impregnating treatment and paraffin embedding of tissue piece (3) in an extremely short period of time.

[Merit (4) in Latest Prior Art]

As a fourth merit in the latest prior art, since the molten paraffin is not polluted by isopropyl alcohol, there is no need of a special pollution check for the recovered isopropyl alcohol and the storage tank.

[Merit (5) in Latest Prior Art]

As a fifth merit in the latest prior art, since it may be advantageous to add the paraffin to the tank in an amount corresponding to the use amount of the paraffin impregnated into the tissue piece, this procedure is very economical.

[Problem (1) in Latest Prior Art]

As a first problem in the latest prior art, since the apparatus adopts a constitution of over-coating of the treating bath (1) by a constant temperature bath (5), the constant temperature bath (5) is bulky and has a large occupied volume, thus, usability and the degree of freedom of installation thereof are extremely poor in a narrow laboratory.

[Problem (2) in Latest Prior Art]

As a second problem in the latest prior art, since the apparatus adopts a constitution of over-coating of the treating bath (1) by a constant temperature bath (5), the weight of the apparatus is larger in the case of adoption of water as a heat medium of the constant temperature bath (5).

[Problem (3) in Latest Prior Art]

As a third problem in the latest prior art, since the apparatus adopts a constitution of over-coating of the treating bath (1) by a constant temperature bath (5) using water or air as a heat medium, the accuracy of temperature control of the bath inside (2) in the treating bath (1) is low.

[Problem (4) in Latest Prior Art]

As a fourth problem in the latest prior art, since the apparatus adopts a constitution of over-coating of the treating bath (1) by a constant temperature bath (5) using water or air as a heat medium and indirect heating and cooling are carried out in this constitution, the heat efficiency is low and electric power consumption is large.

[Problem (5) in Latest Prior Art]

As a fifth problem in the latest prior art, since the apparatus adopts a constitution of over-coating of the treating bath (1) by a constant temperature bath (5) using water or air as a heat medium, there are required exchange of the polluted heat medium, exchange of parts (e.g., nichrome wire) of a complicated apparatus, regulation of a thermostat (e.g., bimetal) and the like, thus, the maintenance is complicated and a trouble tends to occur.

Patent Literature 1: U.S. Pat. No. 5,089,288

SUMMARY OF INVENTION

Subjects to be Solved by Invention

The subject to be solved by the present invention is to solve the above-described problems (1) to (5) of the latest prior art, utilizing the above-described merits (1) to (5) of the latest prior art.

[Subject (1) to be Solved by Present Invention]

When it is taken into consideration that laboratories are generally narrow in our country, the above-described first problem of the latest prior art was particularly important as the subject to be solved (space saving of apparatus).

[Subject (2) to be Solved by Present Invention]

When the operators engaged in the experiment are females or middle and aged persons in view of progress of low birthrate and longevity in advanced countries such as Japan, United States of America and Europe, the above-described second problem of the latest prior art was particularly important as the subject to be solved (weight saving of apparatus).

[Subject (3) to be Solved by Present Invention]

Since a tissue piece as a treatment object is, for example, an internal organ, tumor and protein of human bodies and heat modification thereof should be avoided, the above-described third problem of the latest prior art was particularly important as the subject to be solved (enhancement of accuracy of temperature control of apparatus).

[Subject (4) to be Solved by Present Invention]

In view of the political measure for prevention of global heating as typified by Kyoto Protocol, the above-described fourth problem of the latest prior art was particularly important as the subject to be solved (energy saving).

[Subject (5) to be Solved by Present Invention]

When engineer shortage and steep rise of employment cost and repair cost are taken into consideration in view of progress of low birthrate and longevity in advanced countries such as Japan, United States of America and Europe, the above-described fifth problem of the latest prior art was particularly important as the subject to be solved (achievement of maintenance free owing to minimum part number).

[Subject (6) to be Solved by Present Invention]

In view of the political measure for suppressing ozone hole enlargement by a flon gas as typified by Montreal Protocol, establishment of a novel cooling system using no flon gas was particularly important as the subject to be solved (non-flon cooling technology).

Features for Solving the Subjects

[First Invention]

The first present invention is a tissue piece treating apparatus having a structure in which a treatment liquid (5) or molten paraffin (5') for treating a tissue piece (3) accommodated in a cassette (4) is stored in a bath inside (2) in a treating bath (1), the tissue piece (3) is soaked in the stored treatment liquid (5) or molten paraffin (5'), and the bath inside (2) is irradiated with an ultrasonic wave from an ultrasonic vibrator (6) fixed to or brought into contact with an external wall outside the treating bath (1) to promote the impregnation of the treatment liquid (5) or molten paraffin (5') into the tissue piece (3) or to promote the treatment of the tissue piece (3);

wherein the tissue piece treating apparatus comprises an input means for setting the temperature of the treatment liquid (5) or molten paraffin (5') stored in the bath inside (2) at a desired maintenance temperature, an automatic controlling means for feeding back the actual temperature of the treatment liquid (5) or molten paraffin (5') stored in the bath inside (2) detected by a temperature sensor (S) to switch a heating mode and a cooling mode alternately, thereby maintaining the temperature of the treatment liquid (5) or molten paraffin (5') stored in the bath inside (2) at a desired maintenance temperature, a heating means for turning OFF in an air-cooling fan (F) of the ultrasonic vibrator (6) and ON in a plane heater (H) at the heating mode, thereby transferring the heat generated by the ultrasonic vibrator (6) and the plane heater (H) to the bath inside (2) to heat the bath inside (2), and a cooling means for turning ON in the air-cooling fan (F) of the ultrasonic vibrator (6) and OFF in the plane heater (H) at the cooling mode, thereby blocking the heat transfer from the ultrasonic vibrator (6) and the plane heater (H) to the bath inside (2) to cool the bath inside (2); and wherein the tissue piece treating apparatus has a function of suppressing excessive heating of the tissue piece (3) to suppress the heat modification of the tissue piece (3), by performing automatic control for maintaining the temperature of the treatment liquid (5) or molten paraffin (5') stored in the bath inside (2) at a desired maintenance temperature by automatically switching the heating mode and the cooling mode.

[Second Invention]

The second present invention is the tissue piece treating apparatus according to [First invention], wherein the treatment liquid (5) is at least one selected from the group consisting of a fixing agent, dehydrating agent, degreasing agent and intermediate agent.

[Third Invention]

The third present invention is the tissue piece treating apparatus according to [First invention], wherein the ultrasonic vibrator (6) oscillates an ultrasonic wave of 10 kHz or more and 80 kHz or less.

[Fourth Invention]

The fourth present invention is the tissue piece treating apparatus according to [First invention], wherein the maintenance temperature of the treatment liquid (5) or molten paraffin (5') stored in the bath inside (2) is a temperature of 30° C. or higher and 80° C. or lower.

[Fifth Invention]

The fifth present invention is the tissue piece treating apparatus according to [First invention], wherein the accuracy of the maintenance temperature of the treatment liquid (5) or molten paraffin (5') stored in the bath inside (2) is within the temperature range of ±2° C. based on the desired maintenance temperature.

[First Characteristic Feature of Tissue Piece Treating Apparatus of the Present Invention]

The first characteristic feature of the tissue piece treating apparatus of the present invention is to comprise an input means for setting the temperature of the treatment liquid (5) or molten paraffin (5') stored in the bath inside (2) at a desired maintenance temperature; and an automatic controlling means for feeding back the actual temperature of the treatment liquid (5) or molten paraffin (5') stored in the bath inside (2) detected by a temperature sensor (S) to switch a heating mode and a cooling mode alternately, thereby maintaining the temperature of the treatment liquid (5) or molten paraffin (5') stored in the bath inside (2) at a desired maintenance temperature.

[Second Characteristic Feature of Tissue Piece Treating Apparatus of the Present Invention]

The second characteristic feature of the tissue piece treating apparatus of the present invention is to comprise a heating means for turning OFF in an air-cooling fan (F) of the ultrasonic vibrator (6) and ON in a plane heater (H) at the heating mode, thereby transferring the heat generated by the ultrasonic vibrator (6) and the plane heater (H) to the bath inside (2) to heat the bath inside (2).

[Third Characteristic Feature of Tissue Piece Treating Apparatus of the Present Invention]

The third characteristic feature of the tissue piece treating apparatus of the present invention is to comprise a cooling means for turning ON in the air-cooling fan (F) of the ultrasonic vibrator (6) and OFF in the plane heater (H) at the cooling mode, thereby blocking the heat transfer from the ultrasonic vibrator (6) and the plane heater (H) to the bath inside (2) to cool the bath inside (2)

[Fourth Characteristic Feature of Tissue Piece Treating Apparatus of the Present Invention]

The fourth characteristic feature of the tissue piece treating apparatus of the present invention is to have a function of suppressing excessive heating of the tissue piece (3) to suppress the heat modification of the tissue piece (3), by using the above-described first to third features.

[Treatment Liquid]

The treatment liquid used in the tissue piece treating apparatus of the present invention is at least one selected from the group consisting of a fixing agent, dehydrating agent, degreasing agent and intermediate agent.

The first to third treatment liquids disclosed in the latest prior art (U.S. Pat. No. 5,089,288) can be adopted, and formalin can be used as the fixing agent, ethanol can be used as the dehydrating or degreasing agent, and xylene can be used as the intermediate agent.

[Molten Paraffin]

The molten paraffin used in the tissue piece treating apparatus of the present invention is the same as disclosed in the latest prior art (U.S. Pat. No. 5,089,288).

[Ultrasonic Vibrator]

The ultrasonic vibrator used in the tissue piece treating apparatus of the present invention oscillates an ultrasonic wave of, preferably, 10 to 80 kHz. In the latest prior art (U.S. Pat. No. 5,089,288), the preferable frequency of the ultrasonic wave oscillated by the ultrasonic vibrator is 35 to 50 kHz, however, in the present invention, the preferable frequency of the ultrasonic wave oscillated by the ultrasonic vibrator is 10 to 80 kHz. The number of the ultrasonic vibrator used in the tissue piece treating apparatus of the present invention is not particularly restricted. For irradiating a tissue piece uniformly with an ultrasonic wave, a plurality of ultrasonic vibrators can be used. When three or more ultrasonic vibrators are used, the arrangement thereof is not particularly restricted, and it may be in the form of straight line, circumference, elliptic circumference or flying goose formation.

[Maintenance Temperature of Treatment Liquid or Molten Paraffin]

The maintenance temperature of the treatment liquid or molten paraffin stored in the bath inside in the tissue piece treating apparatus of the present invention is preferably 30° C. to 80° C., more preferably 40° C. to 70° C., further preferably 50° C. to 60° C., most preferably 60° C.

[Accuracy of Maintenance Temperature of Treatment Liquid or Molten Paraffin]

The accuracy of the maintenance temperature of the treatment liquid or molten paraffin stored in the bath inside in the tissue piece treating apparatus of the present invention is preferably ±2° C., more preferably ±1° C., further preferably ±0.8° C., most preferably ±0.5° C.

[Constitution of Tank in Tissue Piece Treating Apparatus of the Present Invention]

Regarding the constitution of a tank in the tissue piece treating apparatus according to the present invention, the first to third treatment liquids can be adopted, and formalin can be used as the fixing agent, ethanol can be used as the dehydrating or degreasing agent, and xylene can be used as the intermediate agent, as same as the embodiments disclosed in the latest prior art (U.S. Pat. No. 5,089,288).

[Examples of Use of Tissue Piece Treating Apparatus of the Present Invention]

The examples of use of the tissue piece treating apparatus of the present invention is the same as the examples disclosed in the latest prior art (U.S. Pat. No. 5,089,288). That is, when the first to third treatment liquids disclosed in the latest prior art (U.S. Pat. No. 5,089,288) are adopted, the tissue piece treatment procedure includes a fixing treatment of a tissue piece, a first dehydrating treatment of a tissue piece, a second dehydrating treatment of a tissue piece, a third complete dehydrating treatment of a tissue piece, a paraffin impregnating treatment of a tissue piece, recovery of a molten paraffin, fabrication of a paraffin block of a tissue piece and the like, and is the same as in the latest prior art (U.S. Pat. No. 5,089, 288).

If ethanol is used as the dehydrating or degreasing agent, an intermediate treatment (treatment conducted between dehydrating an degreasing treatments and a paraffin impregnating treatment) is carried out using xylene or isopropyl alcohol as the intermediate agent, then, a paraffin impregnating treatment of a tissue piece, recovery of a molten paraffin, fabrication of a paraffin block of a tissue piece, and the like are carried out.

Effects of the Invention

Effect (1) of the Present Invention

The first effect by the present invention is a capability of realizing remarkable space saving which is particularly significant in a narrow laboratory.

Effect (2) of the Present Invention

The second effect by the present invention is a capability of realizing remarkable weight saving of an apparatus which is particularly significant when the operators engaged in the experiment are females or middle and aged persons in view of progress of low birthrate and longevity in advanced countries such as Japan, United States of America and Europe.

Effect (3) of the Present Invention

The third effect by the present invention is a capability of avoiding the heat modification of a tissue piece (e.g., internal organ, tumor and protein of human bodies) by realizing remarkable enhancement of the accuracy of temperature control of an apparatus.

Effect (4) of the Present Invention

The fourth effect by the present invention is to contribute significantly to prevention of global heating by realizing remarkable energy saving in view of the political measure for prevention of global heating as typified by Kyoto Protocol.

Effect (5) of the Present Invention

The fifth effect by the present invention is to contribute to significant reduction of the maintenance cost and repair cost of an apparatus by realizing remarkable achievement of maintenance free in view of progress of low birth-rate and longevity in advanced countries such as Japan, United States of America and Europe.

Effect (6) of the Present Invention

The sixth effect by the present invention is to contribute to suppression of increase of ultraviolet ray sprinkled on the surface of the earth by realizing a non-flon cooling technology by fabricating a novel cooling system using no flow gas in view of the political measure for suppressing ozone hole enlargement by a flon gas as typified by Montreal Protocol.

EXPLANATION OF NUMERAL MARKS

Figure 1:
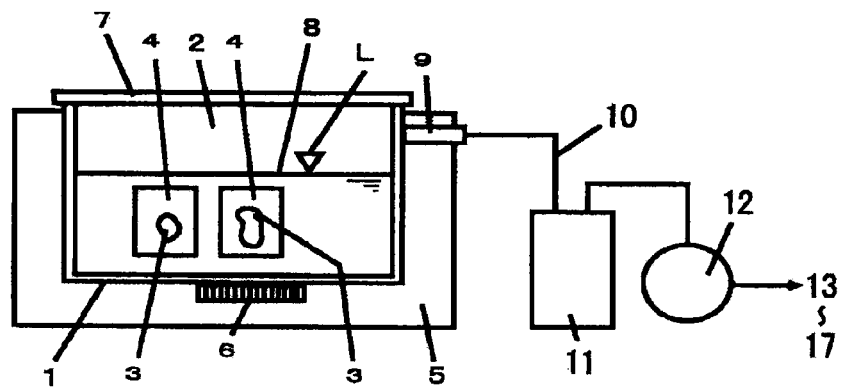
FIG. 1 is a schematic sectional view of an apparatus for specifically illustrating the tissue piece treating apparatus described in the latest prior art (U.S. Pat. No. 5,089,288).

1 treating bath
2 bath inside
3 tissue piece
4 cassette
5 treatment liquid (5 represents a constant temperature bath in the latest prior art)
5' molten paraffin
6 ultrasonic vibrator
7 cover
8 liquid surface
9 connector
10 pipeline
11 filter
12 vacuum pump
13 to 17 tanks
F air-cooling fan
H plane heater
L liquid surface sensor (L represents liquid level in the latest prior art)
S temperature sensor

BEST MODES FOR CARRYING OUT THE INVENTION

Best modes of the tissue piece treating apparatus of the present invention are shown in FIGS. 2 to 8. In FIGS. 2 to 8, (1) represents a treating bath, (2) represents a bath inside, (3) represents a tissue piece, (4) represents a cassette, (5) represents a treatment liquid, (5') represents a molten paraffin, (6) represents an ultrasonic vibrator, (7) represents a cover, (8) represents a liquid surface, (9) represents a connector, (10) represents a pipeline, (11) represents a filter, (12) represents a vacuum pump, (13 to 17) represent tanks, (F) represents an air-cooling fan, (H) represents a plane heater, (L) represents a liquid surface sensor and (S) represents a temperature sensor. The treatments and paraffin impregnating treatment of the tissue piece (3) are all carried out in the bath inside (2) of the treating bath (1).

Figure 2:
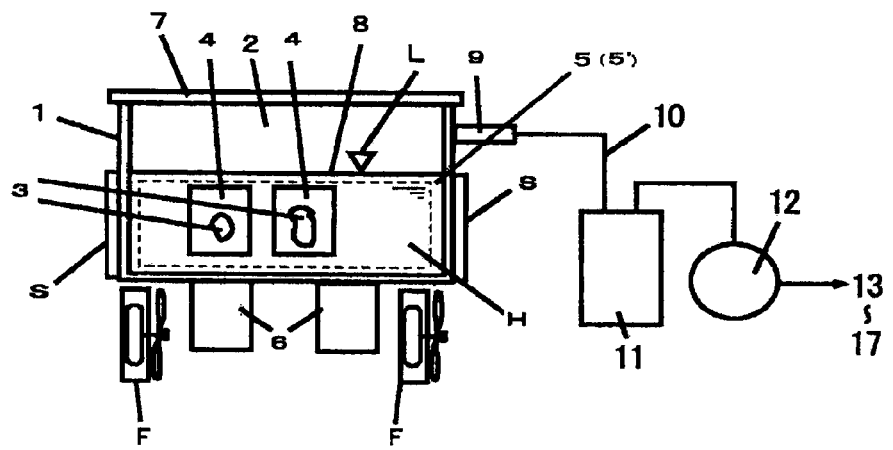
FIG. 2 is a schematic sectional view of an apparatus for specifically illustrating the tissue piece treating apparatus described in the present claims.

FIG. 2 is a schematic sectional view of an apparatus for specifically illustrating the tissue piece treating apparatus described in the present claims.

Figure 3:
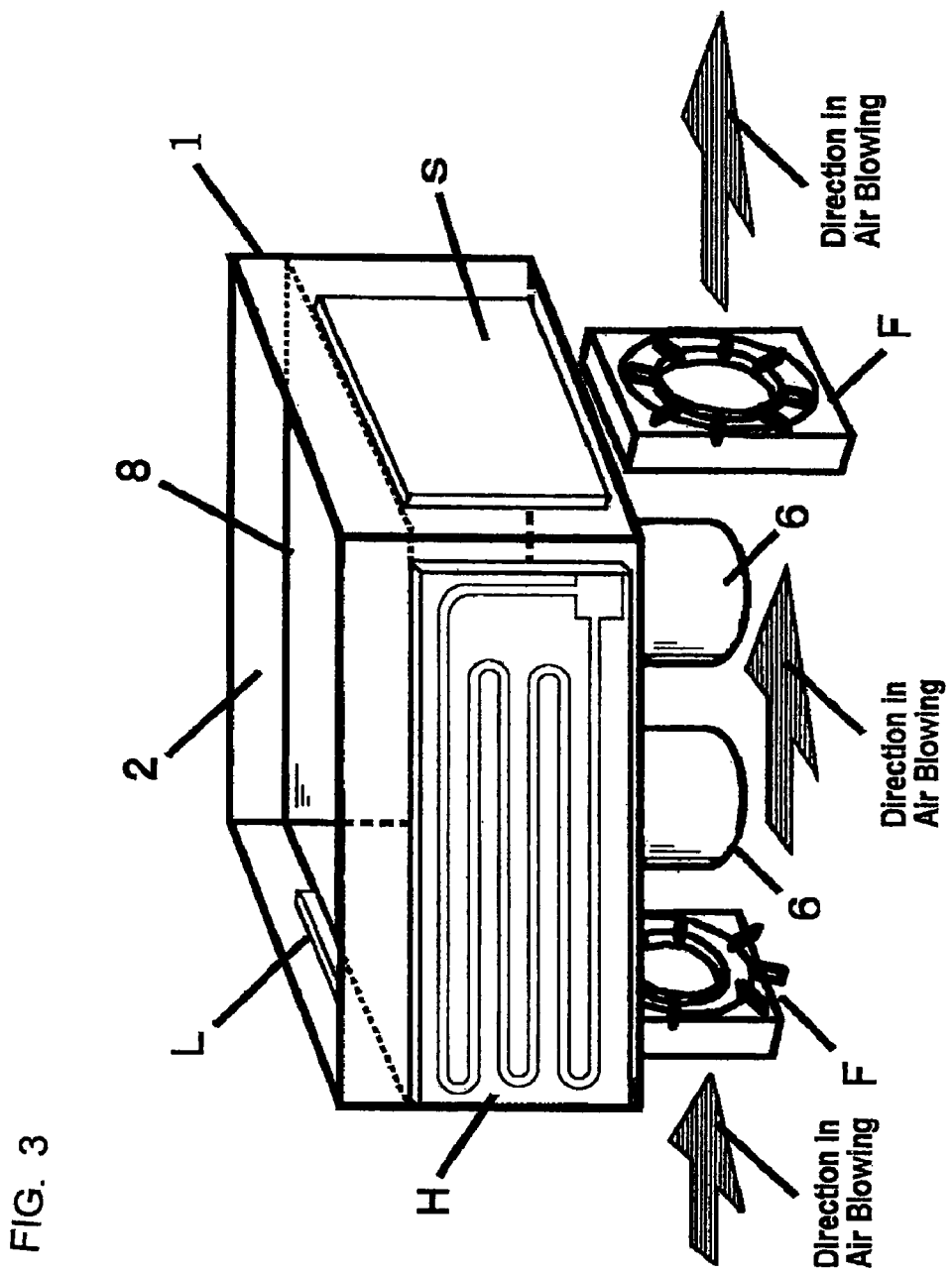
FIG. 3 is a perspective view of an apparatus for specifically illustrating the tissue piece treating apparatus of the present invention.

FIG. 3 is a perspective view of an apparatus for specifically illustrating the tissue piece treating apparatus of the present invention.

Figure 4:
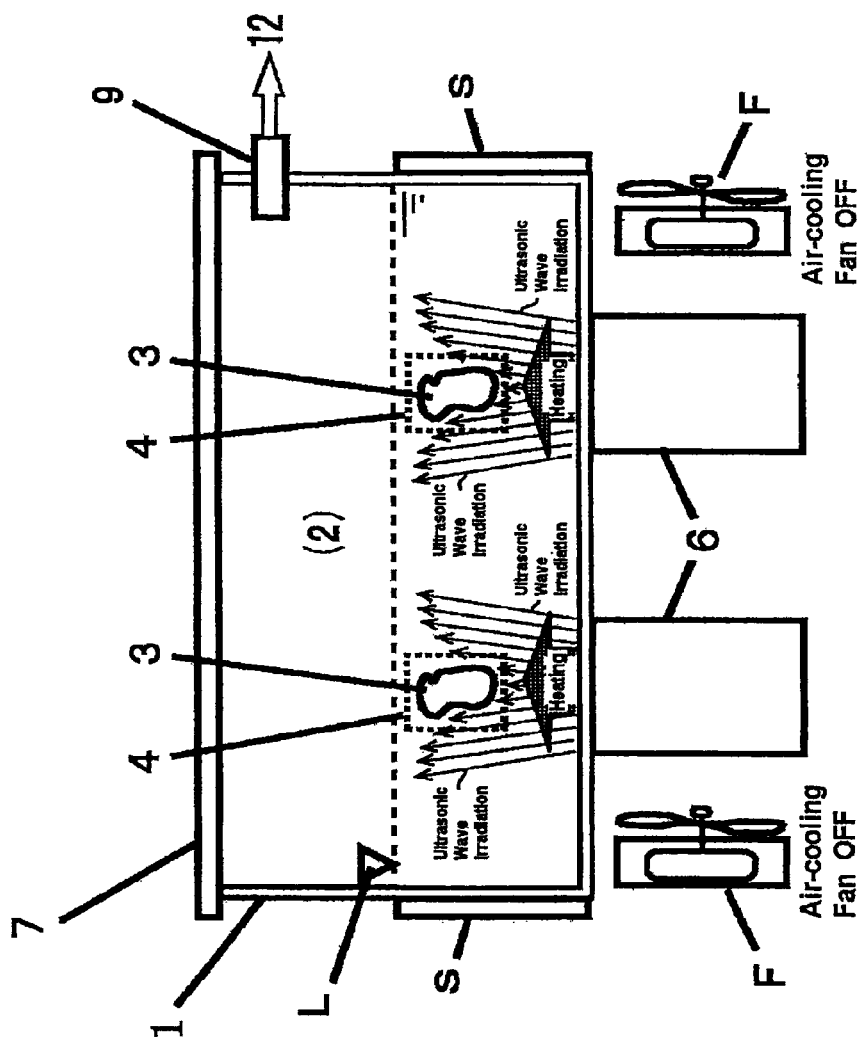
FIG. 4 is a schematic view showing heat transfer from an ultrasonic vibrator at a heating mode of the tissue piece treating apparatus of the present invention.

FIG. 4 is a schematic view showing heat transfer from an ultrasonic vibrator in a heating mode of the tissue piece treating apparatus of the present invention.

Figure 5:
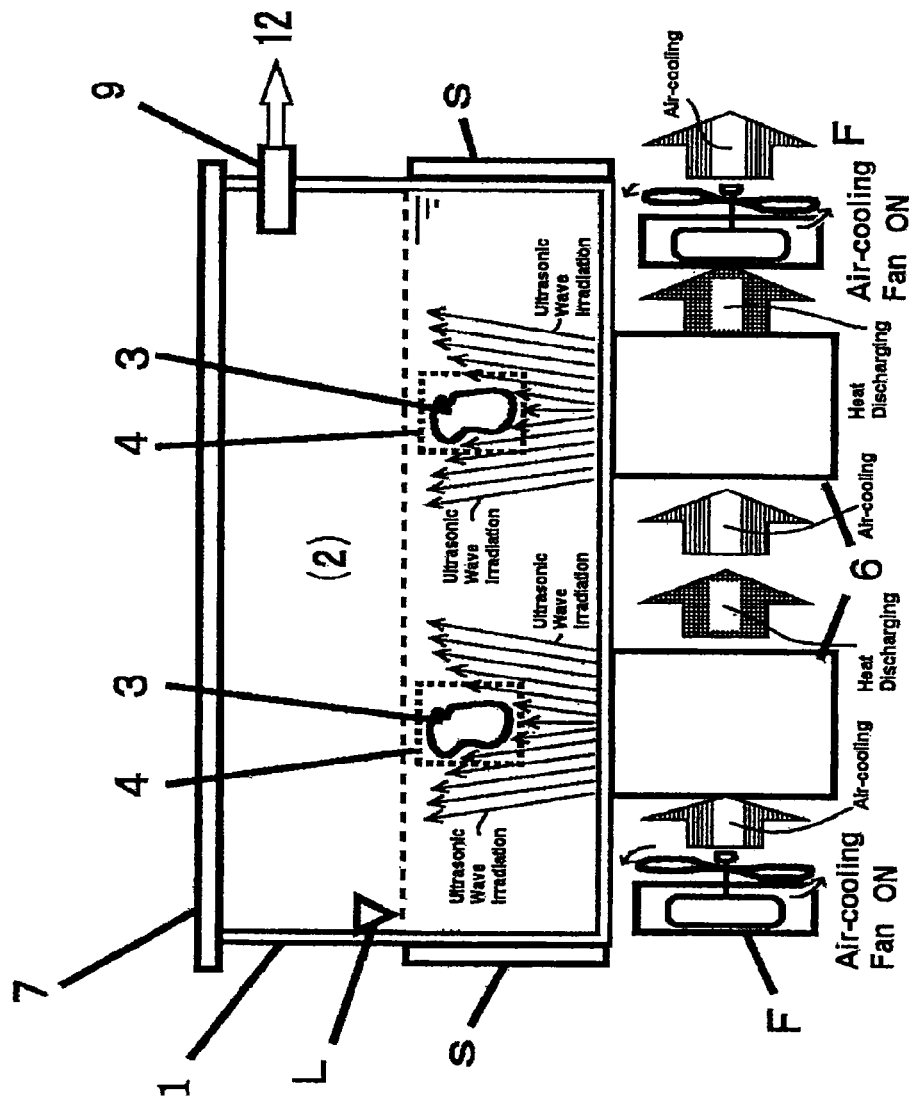
FIG. 5 is a schematic view showing heat transfer from an ultrasonic vibrator at a cooling mode of the tissue piece treating apparatus of the present invention.

FIG. 5 is a schematic view showing heat transfer from an ultrasonic vibrator in a cooling mode of the tissue piece treating apparatus of the present invention.

Figure 6:
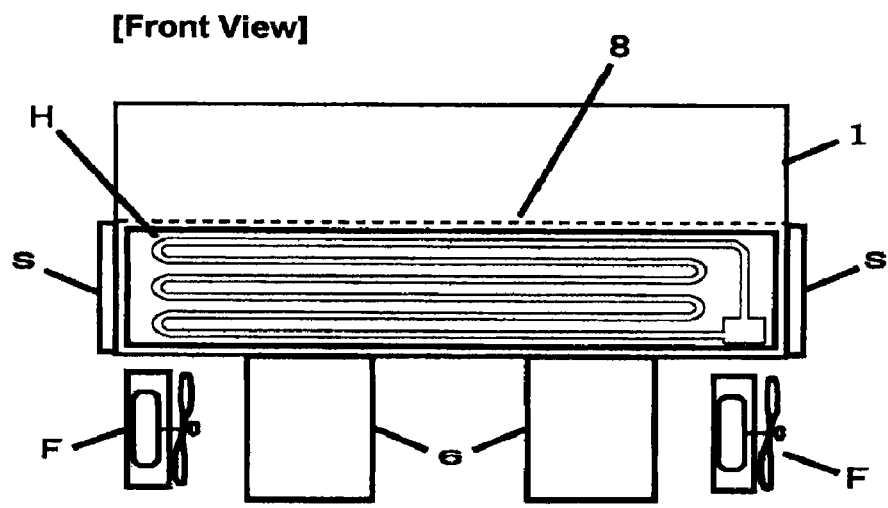
FIG. 6 is a front view of the tissue piece treating apparatus of the present invention.

FIG. 6 is a front view of the tissue piece treating apparatus of the present invention.

Figure 7:
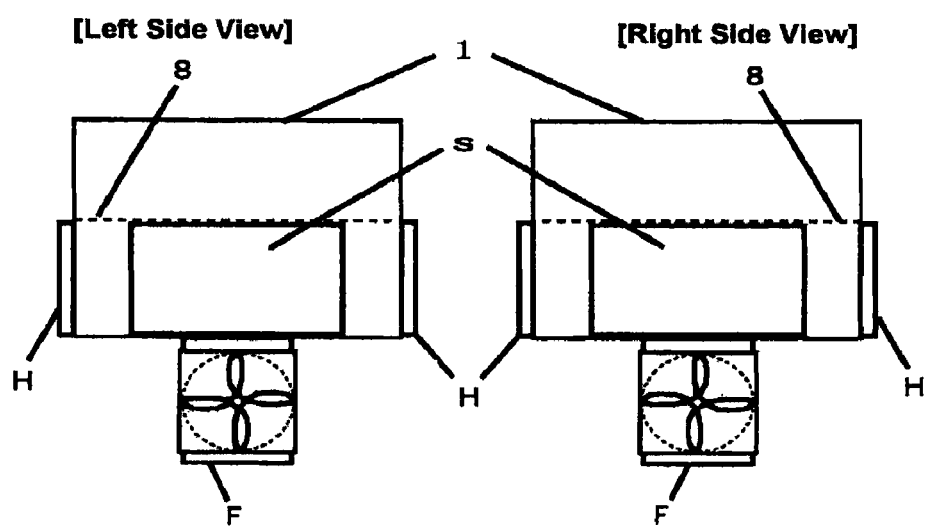
FIG. 7 is a side view of the tissue piece treating apparatus of the present invention.

FIG. 7 is a side view of the tissue piece treating apparatus of the present invention.

Figure 8:
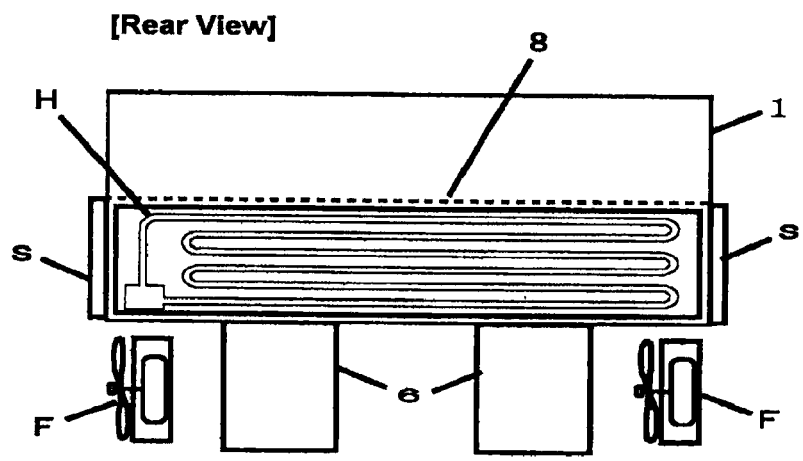
FIG. 8 is a rear view of the tissue piece treating apparatus of the present invention.

FIG. 8 is a rear view of the tissue piece treating apparatus of the present invention.

EXAMPLES

Example 1

A tissue piece treating apparatus having a basic structure shown in FIG. 2 was fabricated.

The outer dimensions of the apparatus included a width of 190 mm, a height of 120 mm and a length of 120 mm and the volume thereof was 2736 $cm^3$.

The outer dimensions of the treating bath included a width of 160 mm, a height of 70 mm and a length of 140 mm and the treating bath was made of stainless steel and had a thickness of 2.0 mm.

Comparative Example 1

A tissue piece treating apparatus having a basic structure shown in FIG. 1 was fabricated.

The outer dimensions of the apparatus included a width of 220 mm, a height of 120 mm and a length of 160 mm and the volume thereof was 4224 $cm^3$.

The treating bath was the same as in Example 1 and the outer dimensions thereof included a width of 160 mm, a height of 70 mm and a length of 140 mm and the treating bath was made of stainless steel and had a thickness of 2.0 mm.

The treating bath was jacked (over-coated) by a water bath made of an acryl plate using water as a heat medium, and temperature control was performed using an immersion heater, stirrer and thermostat.

Comparative Example 2

A tissue piece treating apparatus having a basic structure shown in FIG. 1 was fabricated.

The outer dimensions of the apparatus included a width of 220 mm, a height of 120 mm and a length of 160 mm and the volume thereof was 4224 $cm^3$.

The treating bath was the same as in Example 1 and the outer dimensions thereof included a width of 160 mm, a height of 70 mm and a length of 140 mm and the treating bath was made of stainless steel and had a thickness of 2.0 mm.

The treating bath was jacked (over-coated) by a water bath made of an acryl plate using air as a heat medium, and temperature control was performed using a portable hair drier and thermostat.

Comparative Example 3

An apparatus was fabricated by removing the air-cooling fan from the tissue piece treating apparatus having a basic structure shown in FIG. 2 (Example 1) while leaving the plane heater.

Comparative Example 4

An apparatus was fabricated by removing the plane heater from the tissue piece treating apparatus having a basic structure shown in FIG. 2 (Example 1) while leaving the air-cooling fan.

[Comparison of Response of Temperature Control]

Figure 9:
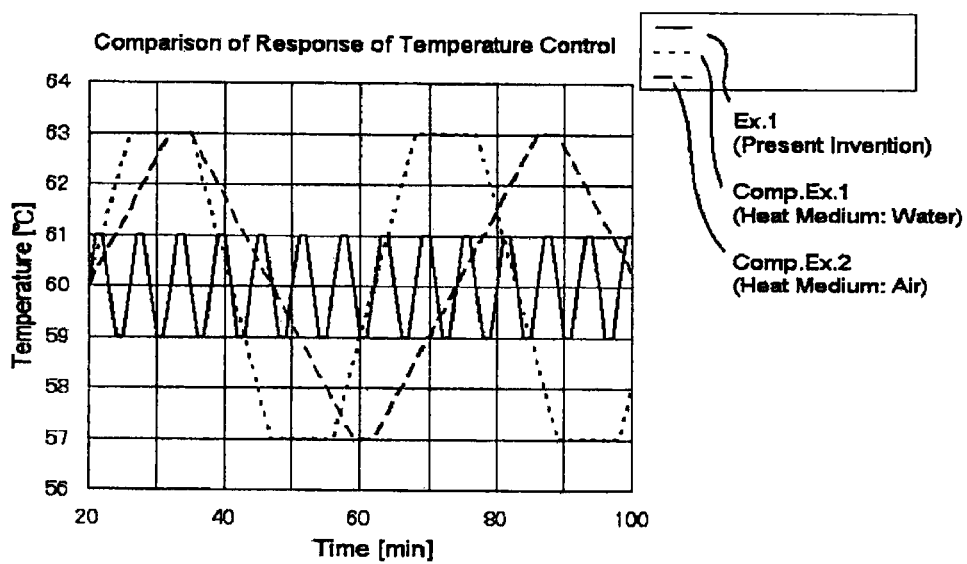
FIG. 9 is a graph showing comparison of response of temperature control of the tissue piece treating apparatus fabricated in Example 1, the tissue piece treating apparatus fabricated in Comparative Example 1 and the tissue piece treating apparatus fabricated in Comparative Example 2.

FIG. 9 shows comparison of response of temperature control in Example 1, Comparative Example 1 and Comparative Example 2.

In the case of Example 1, the accuracy of temperature control was remarkably higher as compared with the cases of Comparative Example 1 and Comparative Example 2.

Comparison of Performance of Treating Apparatus

Table 1 shows the treating apparatus total weight [kg], the treating apparatus total volume [cm³], the heater output [W] and the temperature control area strength [° C.×min] for the tissue piece treating apparatus fabricated in Example 1, the tissue piece treating apparatus fabricated in Comparative Example 1 and the tissue piece treating apparatus fabricated in Comparative Example 2.

The temperature control area strength [° C.×min] is an area strength [° C.×min] as a criterion of the temperature control accuracy read from the graph of FIG. 9.

TABLE 1

|  | Treating apparatus total weight [kg] (%) | Treating apparatus total volume [cm³] (%) | Heater Output [W] (%) | Temperature control area strength [° C.×min] (%) |
|---|---|---|---|---|
| Example 1 (present invention | 2.2 (46) | 2736 (65) | 155 (52) | 53.5 (30) |
| Comparative Example 1 (heat medium: water) | 4.8 (100) | 4224 (100) | 300 (100) | 176 (100) |
| Comparative Example 2 (heat medium: air) | 2.4 (50) | 4224 (100) | 300 (100) | 135 (77) |

As shown in Table 1, the total volume was 4224 cm³ in Comparative Example 1 and Comparative Example 2, and 2736 cm³ in Example 1, the comparison showing a capability of space saving.

The weight was 4.8 kg in Comparative Example 1 and 2.2 kg in Example 1, the comparison showing a capability of weight saving.

The heater output was 300 W in Comparative Example 1 and Comparative Example 2 and 155 W in Example 1, the comparison showing a capability of energy saving.

Since temperature control is performed using water or air as a heat medium in Comparative Example 1 and Comparative Example 2 as shown in FIG. 1, direct access to the ultrasonic vibrator and treating bath for repair is difficult. Further, exchange of a heat medium due to the life duration of the medium is also necessary.

In contrast, the ultrasonic vibrator and the treating bath, air-cooling fan, plane heater, temperature sensor and the like are not jacketed (over-coated) in Example 1 as shown in FIG. 2, the direct access is possible, thus, repair and parts exchange thereof are easy.

[Comparison of Case Using Only Plane Heater And Case Using Only Air-Cooling Fan]

Figure 10:
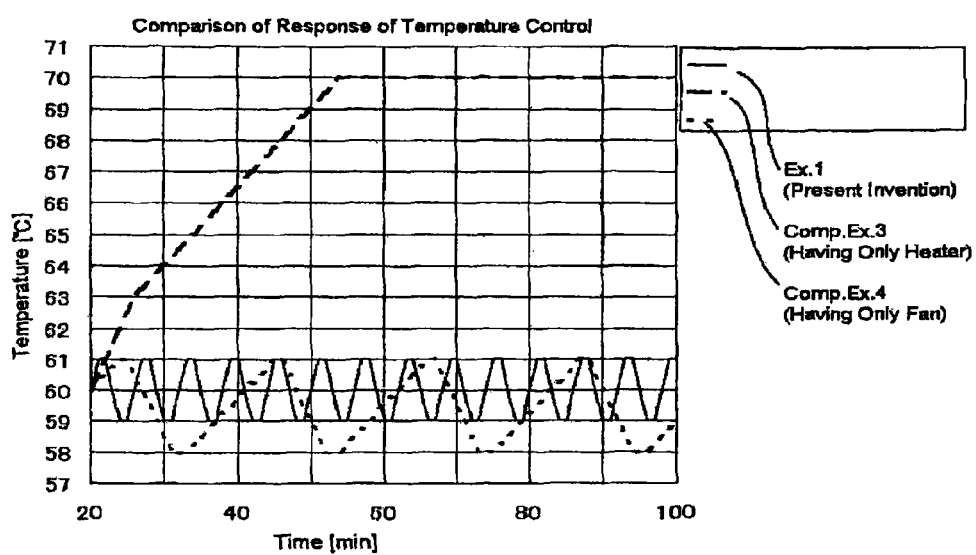
FIG. 10 is a graph showing comparison of response of temperature control of the tissue piece treating apparatus fabricated in Example 1, an apparatus (Comparative Example 3) obtained by removing the air-cooling fan while leaving the plane heater in the tissue piece treating apparatus of Example 1 and an apparatus (Comparative Example 4) obtained by removing the plane heater while leaving the air-cooling fan in the tissue piece treating apparatus of Example 1.

FIG. 10 shows comparison of response of temperature control of the tissue piece treating apparatus fabricated in Example 1, an apparatus (Comparative Example 3) obtained by removing the air-cooling fan while leaving the plane heater in the tissue piece treating apparatus fabricated in Example 1 and an apparatus (Comparative Example 4) obtained by removing the plane heater while leaving the air-cooling fan in the tissue piece treating apparatus (Example 1) fabricated in Example 1.

As apparent from FIG. 10, the accuracy of temperature control was poor in both Comparative Example 3 and Comparative Example 4.

In the case of Example 1 having both the plane heater and the air-cooling fan, however, the accuracy of temperature control was high because of a synergistic effect of the plane heater and the air-cooling fan.

INDUSTRIAL APPLICABILITY

Excessive heating of a tissue piece is suppressed to suppress the heat modification of the tissue piece, by maintaining the temperature in the treating bath at a constant temperature with high accuracy by automatic control and shortening the treatment time by irradiation with an ultrasonic wave.

The invention claimed is:

1. A tissue piece treating apparatus having a structure in which
   a treatment liquid or molten paraffin for treating a tissue piece accommodated in a cassette is stored in a bath inside in a treating bath,
   the tissue piece is soaked in the stored treatment liquid or molten paraffin, and
   the bath inside is irradiated with an ultrasonic wave from an ultrasonic vibrator fixed to or brought into contact with an external wall outside the treating bath to promote the impregnation of the treatment liquid or molten paraffin into the tissue piece or to promote the treatment of the tissue piece;
   wherein the tissue piece treating apparatus comprises
   an input means for setting the temperature of the treatment liquid or molten paraffin stored in the bath inside at a desired maintenance temperature,
   an automatic controlling means for feeding back the actual temperature of the treatment liquid or molten paraffin stored in the bath inside detected by a temperature sensor to switch a heating mode and a cooling mode alternately, thereby maintaining the temperature of the treatment liquid or molten paraffin stored in the bath inside at a desired maintenance temperature,
   a heating means for turning OFF in an air-cooling fan of the ultrasonic vibrator and ON in a plane heater at the heating mode, thereby transferring the heat generated by the ultrasonic vibrator and the plane heater to the bath inside to heat the bath inside, and a cooling means for turning ON in the air-cooling fan of the ultrasonic vibrator and OFF in the plane heater at the cooling mode, thereby blocking the heat transfer from the ultrasonic vibrator and the plane heater to the bath inside to cool the bath inside; and wherein the tissue piece treating apparatus has a function of suppressing excessive heating of the tissue piece to suppress the heat modification of the tissue piece, by performing automatic control for maintaining the temperature of the treatment liquid or molten paraffin stored in the bath inside at a desired maintenance temperature by automatically switching the heating mode and the cooling mode.

2. The tissue piece treating apparatus according to claim 1, wherein the treatment liquid is at least one selected from the group consisting of a fixing agent, dehydrating agent, degreasing agent and intermediate agent.

3. The tissue piece treating apparatus according to claim 1, wherein the ultrasonic vibrator oscillates an ultrasonic wave of 10 kHz or more and 80 kHz or less.

4. The tissue piece treating apparatus according to claim 1, wherein the maintenance temperature of the treatment liquid or molten paraffin stored in the bath inside is a temperature of 30° C. or higher and 80° C. or lower.

5. The tissue piece treating apparatus according to claim 1, wherein the accuracy of the maintenance temperature of the treatment liquid or molten paraffin stored in the bath inside is within the temperature range of ±2° C. based on the desired maintenance temperature.

\* \* \* \* \*